(12) United States Patent
Jackson et al.

(10) Patent No.: US 6,458,082 B1
(45) Date of Patent: Oct. 1, 2002

(54) SYSTEM AND METHOD FOR THE DISPLAY OF ULTRASOUND DATA

(75) Inventors: John I. Jackson, Menlo Park; Joan C. Main, Mountain View; Janice L. Marshall, Sunnyvale, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/408,418

(22) Filed: Sep. 29, 1999

(51) Int. Cl.[7] .................................................. A61B 8/00
(52) U.S. Cl. ...................................................... 600/441
(58) Field of Search ................................ 600/440, 447, 600/441, 445, 449, 443; 128/916; 382/294

(56) References Cited

U.S. PATENT DOCUMENTS

| | | | |
|---|---|---|---|
| 5,148,810 A | 9/1992 | Maslak et al. | 128/661.01 |
| 5,235,986 A | 8/1993 | Maslak et al. | 128/661.01 |
| 5,261,408 A | 11/1993 | Maslak et al. | 128/661.01 |
| 5,497,776 A | * 3/1996 | Yamazaki et al. | 600/445 |
| 5,682,895 A | * 11/1997 | Ishiguro | 600/440 |
| RE35,720 E | 2/1998 | Arenson et al. | 128/660.05 |
| 6,014,473 A | * 1/2000 | Hossack et al. | 382/294 |

OTHER PUBLICATIONS

*Physics and Instrumentation of Diagnostic Medical Ultrasound*, by Peter Fish, pp. 1–189 (1990).
*An Architecture for Rule–Based Visulization,* by Bernice E. Rogowitz and Lloyd A. Treinish, (1993), IEEE Visualisation, pp. 236–243.

* cited by examiner

Primary Examiner—Marvin M. Lateef
Assistant Examiner—Maulin Patel
(74) Attorney, Agent, or Firm—Brinks Hofer Gilson & Lione (57) ABSTRACT

A system and method for converting 2-D ultrasound data into a 2-D display image. The system and method input a 2-D ultrasound data set, transform the 2-D ultrasound data set into a mathematical 3-D data set, and transform the mathematical 3-D data set into an altered 2-D data set. Another preferred embodiment of the invention involves generating a mathematical surface, such that the height of the mathematical surface is based on a first component of an ultrasound signal in a 2-D ultrasound data set; mapping the mathematical surface to points on a 2-D plane; assigning a color value to each point based on a second component of the ultrasound signal; and displaying the mapped mathematical surface with the assigned color values on a 2-D display device.

69 Claims, 4 Drawing Sheets

(OBSERVER)

SYSTEM AND METHOD FOR THE DISPLAY OF ULTRASOUND DATA

BACKGROUND OF THE INVENTION

1. Field of Invention

This invention relates to an improved system and method for acquiring two-dimensional (2-D) diagnostic ultrasound image information, and more specifically, relates to displaying the image information in an easier-to-interpret format.

2. Description of the Prior Art

There is growing interest in 2-D ultrasound images for medical applications. An ultrasound system acquires an ultrasound signal by converting an acoustical pressure wave to an electronic voltage. The amplitude of the signal is dependent on a number of factors, including reflectivity or radiation amplitude of an object in the field of view where ultrasound data is being acquired. The theory of medical ultrasound imaging is clearly discussed in *Physics and Instrumentation of Diagnostic Medical Ultrasound,* by Peter Fish, pp. 1–189 (1990).

Ultrasound systems typically generate a 2-D image, where each pixel location within the image corresponds to a spatially localized region being imaged. The brightness or color that is assigned to each pixel in the image is a function of the amplitude of the signal that corresponds to a specific localized region. This is commonly referred to as B-mode ultrasound imaging, and typically uses gray-scale pixels.

What is needed is an improved ultrasound system and method to display 2-D images of important anatomical structures in a manner that is more easily interpreted than with conventional imaging using pixel brightness.

SUMMARY OF THE INVENTION

The object of the present invention is to provide an improved system and method to display 2-D images of important anatomical structures in a manner that is more easily interpreted than with conventional 2-D images using pixel brightness.

A first aspect of the invention involves a system and method for inputting a 2-D ultrasound data set, transforming the 2-D ultrasound data set into a mathematical 3-D data set, and transforming the mathematical 3-D data set into an altered 2-D data set.

A second aspect of the invention involves a method and system for generating a mathematical surface from a single plane of an ultrasound data set, wherein the height of the surface is based on a first component of an ultrasound signal; mapping the mathematical surface to points on a 2-D plane; assigning a color value to each point based on a second component of the ultrasound signal; and displaying the mapped mathematical surface with the assigned color values on a 2-D display device.

These and other objects and advantages of the invention will become apparent to those skilled in the art from the following detailed description of the invention and the accompanying drawings.

BRIEF DESCRIPTION OF THE DRAWINGS

FIG. 1 shows a schematic drawing of an example of an ultrasound system that can be used to carry out the invention.

FIG. 2(*a*) represents a conventional 2-D ultrasound image having a square bright reflector centered in a dark background.

FIG. 2(*b*) represents a mapped mathematical surface of the data of FIG. 2(*a*).

FIG. 6(*a*) is a photograph of a conventional gray-scale B-mode ultrasound image.

FIG. 6(*b*) is a surface-rendered image derived from the conventional B-mode image shown in FIG. 6(*a*).

DETAILED DESCRIPTION OF PREFERRED EMBODIMENTS OF THE INVENTION

Figures 1, 2A, 2B:
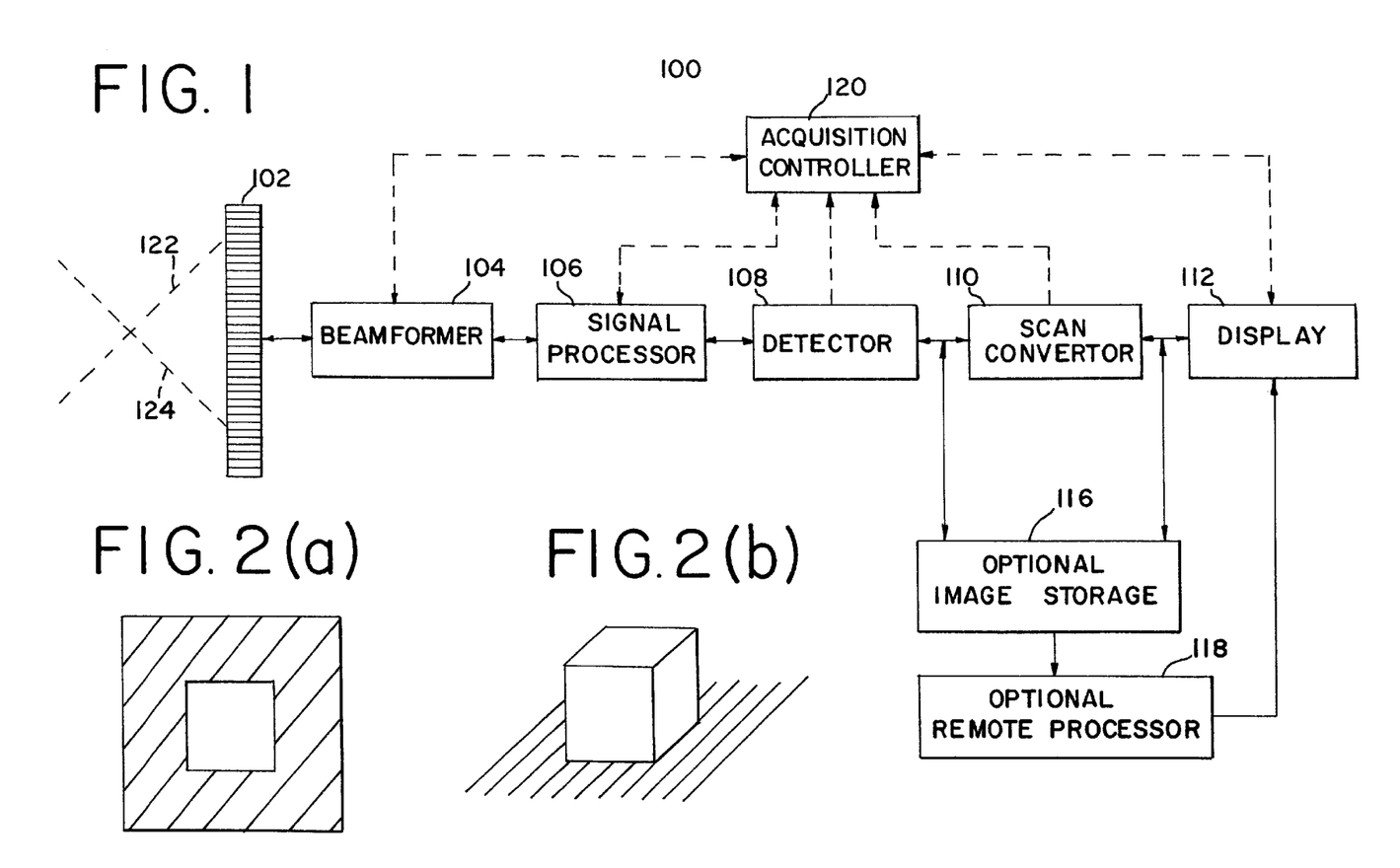

FIG. 1 shows a schematic drawing of an example of an ultrasound system 100 that can be used to carry out the invention. System 100 includes a data path comprising transducer 102, beamformer 104, signal processor 106, detector 108, scan converter 110, display device 112, optional image storage 116 and optional remote processor 118. Acquisition controller 120 directly outputs control signals and receives status signals for the control of the data path components: beamformer 104, signal processor 106, detector 108, scan converter 110, and display device 112. Acquisition controller 120 may also coordinate user input. Optional image storage 116 receives input data from the output lines of detector 108 or scan converter 110, and outputs data to scan converter 110, display 112, or optional remote processor 118. Optional remote processor 118 outputs data to display device 112.

Transducer 102 is typically a linear array or phased linear array of piezoelectric elements. However, any commercially available ultrasound imaging transducer can be used with the preferred embodiments of the invention. The ultrasound imaging transducer may be, for example, an ultrasound rotating single crystal transducer, or a 1-D, 1.5-D, or 2-D ultrasound phased array transducer.

Beamformer 104 is constructed in a manner known in the art. Beamformer 104 may optionally comprise separate transmit and receive beamformers. Beamformer 104 produces excitation signals for each or a subset (i.e., a sub-aperture) of the elements of transducer 102. The excitation signals are processed, such as by applying a relative delay or amplitude, to focus ultrasound waveforms along one or more scan lines 122 and 124. The scan lines can be at any of various angles relative to transducer 102, and originate at various locations along, in front of, or behind transducer 102. Variable origin and variable angle acoustic scanning methods and apparatus (which generate Vector® wide view array imaging formats) are disclosed in U.S. Pat. Nos. 5,148,810, 5,235,986, and 5,261,408 to Maslak, et al., which are assigned to the assignee of the present invention and hereby incorporated by reference. The plane defined by two or more scan lines comprises a scan plane.

Transmitted acoustic energy is reflected off structures within a body as echoes, which are detected by the elements of transducer 102, and provided as voltage signals to beamformer 104. Beamformer 104 sums the voltage signals and outputs ultrasound data representative of structures along one or more scan lines.

Signal processor 106 is a construction known in the art, such as a digital signal processor or filtering device for processing the representative ultrasound data. Signal processor 106 can include a B-mode processor and/or a spectral Doppler processor. Alternatively, or in addition, signal processor 106 can estimate the Doppler velocity, energy, and/or variance for each of various points along each scan line; or it can estimate Doppler tissue velocity, energy or acceleration, as described in Reissued U.S. Pat. No. 35,720 to Arenson, et al. These Doppler modalities are effectively referred to as "F-mode" or "color flow" imaging. F-mode images depict a color image of moving blood (or tissue, in the case of Doppler tissue imaging), typically superimposed on a real-time gray-scale B-mode display. Sequences of the B-mode and/or Doppler acoustic or image frame data can be stored in image storage 116.

In a preferred embodiment, signal processor 106 also supports harmonic imaging, i.e., harmonic B-mode images and/or harmonic F-mode images, wherein the received acoustic data is at a harmonic frequency of the transmitted acoustic pulses.

In another embodiment, signal processor 106 also supports M-mode imaging, i.e., TM (time motion) or TP (time position) imaging, including 2-D derived M-mode imaging, which is most often used for cardiac measurements, particularly for detecting abnormalities in the movement of heart valves. A brightness-modulated display is written vertically on the display device 112, and a display line is moved slowly across the display device 112 at a regular rate. Stationary reflectors are indicated by horizontal lines, while a variation in position with time is indicated by the vertical movement of the echo on the display device 112. Moreover, M-mode displays can include both B-mode and F-mode information, and be shown in conjunction with full 2-D B-mode and F-mode displays.

The acoustic data representing areas in the scan plane or along a scan line is provided by signal processor 106 to detector 108 and scan converter 110. The ultrasound data to be used according to the preferred embodiments of the invention can be taken from system 100 anywhere along the data path comprising beamformer 104, signal processor 106, detector 108, and scan converter 110. Embodiments that take the data earlier in the system data path theoretically allow a faster display of data. However, the most preferred embodiment of the invention processes the data received as input to scan converter 110.

Scan converter 110 is a processor or a dedicated circuit for formatting the acoustic data into a Cartesian coordinate system for display as images. For each grid point in the Cartesian coordinate system, the nearest acquired sample data points are interpolated to find the data value corresponding to each grid point. The interpolation algorithm can use a linear or higher order function, such as a higher order polynomial function.

Most preferably, scan converter 110 performs the transformation of the 2-D ultrasound data set into a mathematical 3-D data set and the transformation of the mathematical 3-D data set into an altered 2-D data set for display. In a less preferred embodiment, one or both of these transformations are performed by remote processor 118, which is a separate, stand-alone processor (e.g., a personal computer or workstation).

The most preferred embodiment of the invention displays surface-rendered images on display device 112 in "real time," i.e., as the data is being collected, or at least within five seconds after the 2-D data set acquisition is completed. In other preferred embodiments, the processed image information is displayed on display device 112 at least within twenty seconds after completion of the acquisition of the 2-D data set.

Display device 112 is a monitor, such as a color monitor. The scan converted data representing the scan plane is displayed on display device 112 based on B-mode intensity, Doppler velocity, Doppler energy, Doppler variance, Doppler tissue velocity, energy, or acceleration, spectral Doppler or any combination thereof, and in any combination of fundamental and/or harmonic imaging. Other ultrasound processing modes can be incorporated into the display image, such as M-mode, color M-mode, or color Doppler mode (with or without an underlying B-mode image).

Preferred embodiments of the invention are generally described as either systems or methods to input a 2-D ultrasound data set, transform the 2-D ultrasound data set into a mathematical 3-D data set, and transform the mathematical 3-D data set into an altered 2-D data set. The input 2-D ultrasound data set can be obtained from one frame of 2-D ultrasound data, one frame of data derived from a 3-D ultrasound data set, or one frame of data derived from the ultrasound data corresponding to one or more ultrasound M-mode lines.

Preferably, a first and/or second ultrasound parameter is extracted from the 2-D ultrasound data set and used to create the mathematical 3-D data set, and a color value is applied to each point of the display of the altered 2-D data set. The color value represents either a first and/or a second parameter derived from the 2-D ultrasound data set. This general explanation is further illustrated by specific examples given below.

FIG. 2(a) represents a conventional 2-D ultrasound image having a square bright reflector centered in a dark background.

FIG. 2(b) represents a mapped mathematical surface of the data of FIG. 2(a). The information contained in FIG. 2(b) is represented such that the square bright reflector is displayed as though raised above the dark background, to a height based on the amplitude of the signal generated by the square bright reflector.

Figure 3:
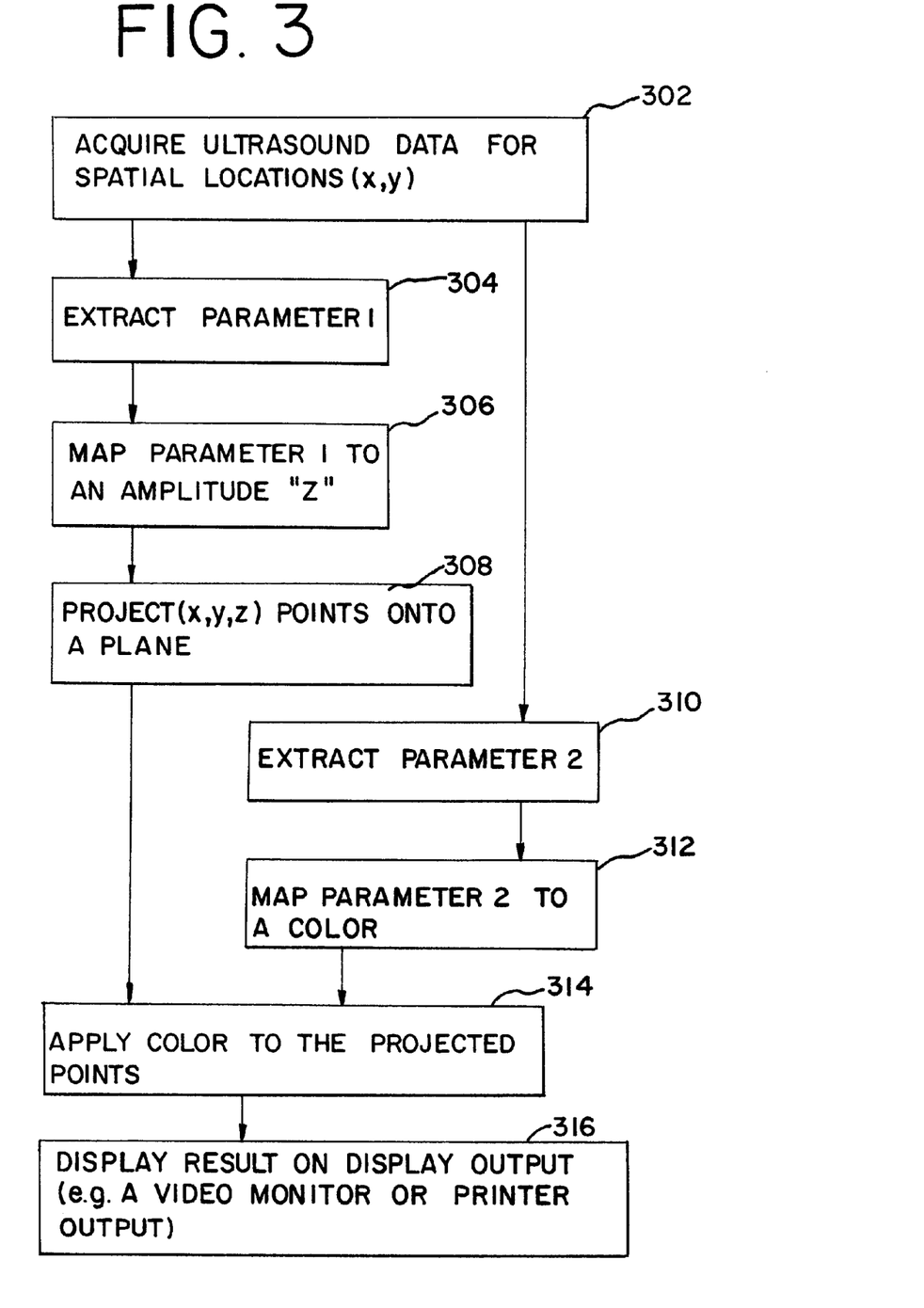
FIG. 3 is a flow chart showing a preferred embodiment of the invention.

FIG. 3 is a flow chart showing a preferred embodiment of the invention. Step 302 is the acquisition of ultrasound data from spatial locations (x, y). Step 304 is the extraction of a first parameter from the ultrasound data. The first parameter can be a function of the signal intensity of B-mode data; or a function of a velocity estimate, variance, or energy of color Doppler data; or any combination thereof. Moreover, the B-mode or color Doppler data can be filtered such that only a subset (sub-band) of the returned frequencies is used to define the parameter. Step 306 is directed to mapping the first parameter to an amplitude "z." Step 308 is the projection of 3-D coordinates (x, y, z) onto a plane. Step 310 is the extraction of a second parameter from the ultrasound data, which can be the same as or different from the first parameter, and selected from the same type of data as described in connection with the first parameter. Step 312 is directed to mapping the second parameter to a color value. This mapping step may be as simple as retrieving a color value from a look-up table; or may include selection of a particular look-up table based on a variable, such as the observer's position, the position of a light source, physical properties attributed to the mathematical surface, and/or geometrical properties of the mathematical surface. Alternatively, the mapping step 312 can be calculated by a processor in or associated with the system, based on any of the foregoing variables. As used herein, "color value" means an RGB or YUV value, or a gray-scale intensity (brightness) value, or any other display characteristic used in a display device, such as a cathode ray tube, flat panel display, or projection display; or means any color or gray-scale combination that is electronically displayed or printed. As used herein, "physical properties" attributed to the mathematical surface include reflectivity, diffusivity, and the like. Step 314 is the application of the color value to the projected points. Step 316 is the display on a display device (e.g., a video monitor or a printer output).

A preferred embodiment of the invention is directed to a display format where the image represents a mathematical surface. The azimuthal and range dimensions are included, as in a conventional display image. For each localized azimuth and range location, two parameters are computed: (1) an amplitude, and (2) a color value. In conventional Cartesian coordinate terminology, the amplitude is considered to be the height, z, of the surface over the (x, y) plane. The height is a function of the amplitude of the ultrasound signal, or of some portion of the ultrasound signal, such as a harmonic, sub-harmonic, fractional harmonic, or ultra-harmonic signal. In another embodiment of the invention, the height is a function of a Doppler signal, optionally including a combination of the energy, velocity, or variance of the Doppler signal.

In another embodiment of the invention, the height is a function of other localized image statistics. For example, regions that rapidly de-correlate, such as might be expected from electronic or thermal noise, could be assigned a first height range. Regions with a correlation consistent with acoustic speckle could be assigned a second height range. Regions that de-correlate very slowly, as might be expected from a smooth reflecting surface, could be assigned a third height range.

For each 3-D coordinate on the mathematical surface, a color value is assigned. The color value is typically a function of the same parameters that were used to compute the amplitude, but the color value could optionally be based on different parameters. In one embodiment of the invention, the color value is a function of the surface amplitude. Alternatively, it could be a function of the amplitude of the ultrasound signal, such as is displayed on ultrasound systems displaying conventional 2-D images. Alternatively, the color value could be based on a more complex function, such as one that includes a light source and/or a reflectivity of the surface. The function could include the relative positions of the light source, the user, and the geometric normal to the surface at each point on the surface.

There are two steps to generating the surface-rendered image. The first step is the mapping of (x, y, f(x, y)) triples (i.e., 3-D coordinates of the mathematical surface) to points on a 2-D (x', y') plane. The second step is determining the color value to assign to each point. In the first step, the user is at a fixed distance and angle away from the surface, or the perspective is drawn for a user who is at an infinite distance away at a fixed angle from the surface. This is a subset of the first case, but it can be generated with a simpler calculation.

Figure 4:
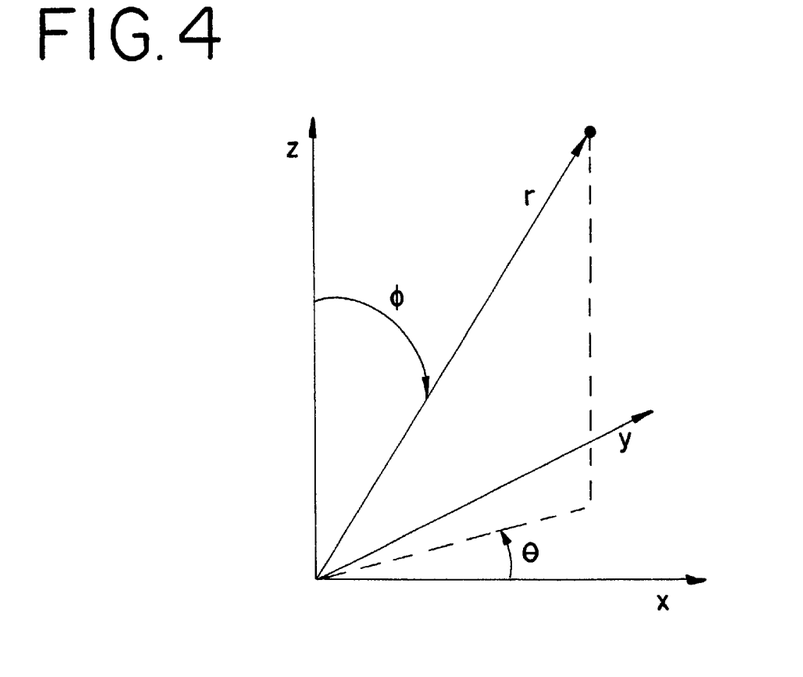
FIG. 4 is drawing of 3-D space showing the relationship between Cartesian (x, y, z) coordinates and spherical (r, θ, φ) coordinates.

FIG. 4 is drawing of 3-D space showing the relationship between Cartesian (x, y, z) coordinates and spherical (r, θ, φ) coordinates. The value of r is the distance from (0, 0, 0) to the point (x, y, z). The value of θ is the angle from the positive x-axis to the point (x, y, 0), measured in the counter-clockwise direction. The value of φ is the angle from the positive z-axis to the point (x, y, z). Any point in a 3-D space can be represented in either Cartesian coordinates or spherical coordinates, but some shapes are more conveniently described as functions of variables expressed in spherical coordinates.

Consider a surface consisting of 3-D coordinate points (x, y, z), where z=f(x, y). Consider a user who views the surface from an angle of (θ, φ). The user views the surface as a projection onto a plane, whose points are located at:

$$\begin{bmatrix} x' \\ y' \end{bmatrix} = \begin{bmatrix} -\sin\theta & \cos\theta & 0 \\ -\cos\theta\cos\phi & -\sin\theta\sin\phi & \sin\phi \end{bmatrix} \begin{bmatrix} x \\ y \\ z \end{bmatrix} \quad (1)$$

If the user is located a finite distance away, at $(r_0, \theta_0, \phi_0)$, in spherical coordinates, but which is $(x_0, y_0, z_0)$, in Cartesian coordinates, where x=r cos θ sin φ, y=r sin θ sin φ, z=r cos φ, then 3-D coordinate points (x, y, z) are mapped by projection to points on a spherical surface, where the user is at the center of the sphere. The points on the sphere are (θ', φ') where $$r' = \sqrt{(x-x_0)^2 + (y-y_0)^2 + (z-z_0)^2},$$

$$\theta' = \arctan\left(\frac{y - y_0}{x - x_0}\right)$$

(where the sign of $(y-y_0)$ and the sign of $(x-x_0)$ are used to generate a value for θ between −π and π, and φ'=arccos $$\phi' = \arccos\left(\frac{z - z_0}{r'}\right)$$

Only the relevant portion of the (θ', φ') plane needs to be shown on the display device (e.g., a video monitor or printer output). A preferred embodiment of the invention groups projected neighboring (x, y) points into sets defining the vertices of quadrilaterals. If convex quadrilaterals cannot be achieved, then triangles are used. In alternative embodiments of the invention, other polygons are used. The quadrilaterals and/or triangles tile the (x, y) plane and do not overlap. Each vertex (x, y) is used by several quadrilaterals (typically four) and/or triangles.

A preferred embodiment of a method according to the invention involves beginning with the set of 3-D coordinate points (x, y, z) furthest from the user and mapping the 3-D coordinate points onto the (x', y') plane or the (θ', φ') surface via equation (1) discussed above. This mapping insures that far-field objects do not obscure objects closer to the user. Then the newly defined polygon is filled with a color value. The entire polygon is one color value, or alternatively, it is based on an interpolation between each color value assigned to each vertex. (The interpolation can be linear, quadrilateral, or a higher order polynomial.) The method then involves proceeding through the remaining sets of points, moving closer and closer to the user until all sets have been mapped.

In a preferred embodiment of the invention, the surface height and pixel color values are derived from the same parameter of the 2-D ultrasound data set, and no new information is mathematically introduced. However, the new display provides a different perspective for the user to view the same data. Cognitively, this enables the user to have a better understanding of the ultrasound data and the structure from which the data was generated. The process of mapping an ultrasound parameter to define the height of a mathematical surface, then mapping the mathematical surface to an altered 2-D data set, is referred to herein as a surface-rendering.

Figure 5:
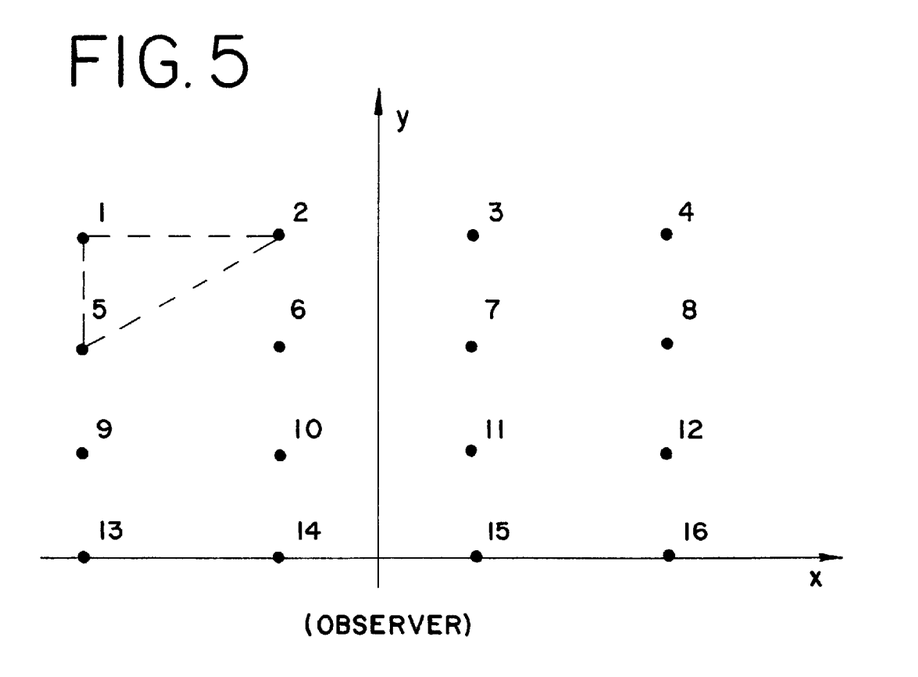
FIG. 5 shows one approach for polygon projection of the (x, y) positions of acquired data.

FIG. 5 shows one approach for polygon projection of the (x, y) positions of acquired data. The points 1 through 16 are positioned on the (x, y) plane for polygon projection for an observer at θ=−90° (i.e., on the negative y-axis). The vertices (1,2,5), (2,5,6), (2,3,6), (3,6,7), (3,4,7), (4,7,8), (5,6,9), . . . will be projected and a color map applied based on the second parameter. The color value applied to the inside of the projected triangle (1,2,5) could be a constant, equal to the color value assigned to the maximum, minimum, or median of the second parameter values at vertices 1, 2, and 5. Preferably, the color value is based on a 2-D interpolation of the second parameter values at the vertices 1, 2, and 5. The interpolation can be simplified by decomposing the 2-D interpolation into two 1-D interpolations. For example, the second parameter can be linearly interpolated from vertex 1 to vertex 2. Interpolating between vertex 5 and the segment from vertex 1 to vertex 2 defines interpolated second parameter values for all points on and inside the triangle (1,2,5). Each color value is then assigned according to the color map.

Figure 6A:
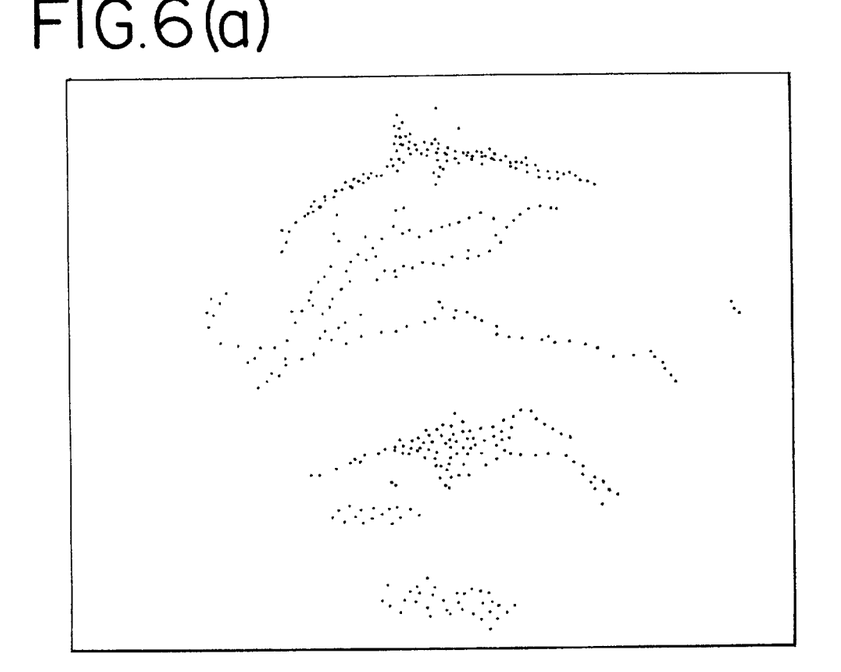

FIG. 6(a) is a photograph of a conventional gray-scale B-mode ultrasound image. Starting at the apex of the sector image, the first bright area corresponds to the anterior wall of a human heart. The dark area immediately above it corresponds to the right ventricle. The second bright area corresponds to the inter-ventricular septum. The second dark area corresponds to the left ventricle and the right side shows a bright "T" shaped structure that corresponds to the aortic valve. The third dark area immediately above the aortic valve is the left atrium. The topmost and most extensive bright area corresponds to the posterior wall of the heart.

Figure 6B:
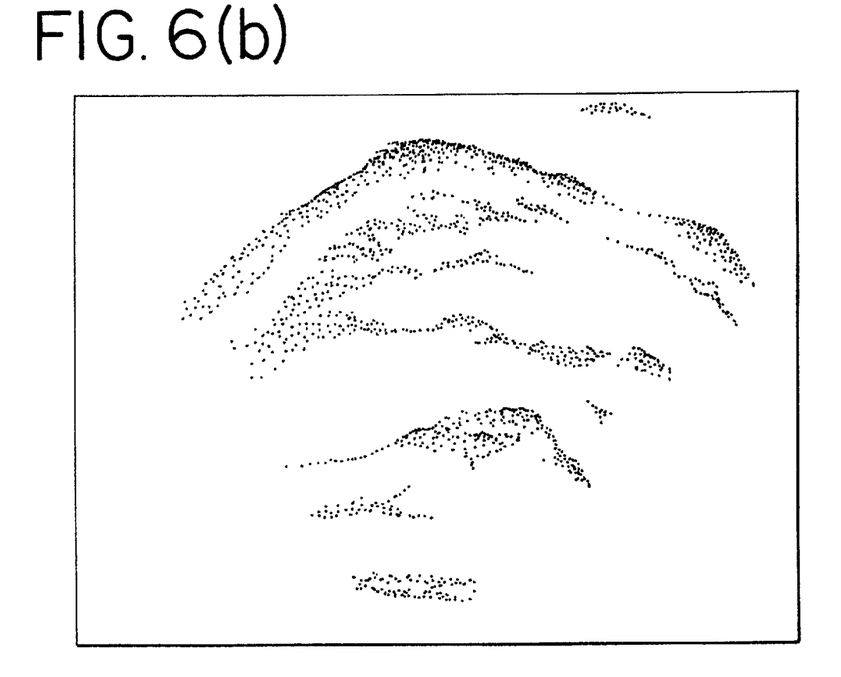

FIG. 6(b) is a surface-rendered image derived from the conventional B-mode image shown in FIG. 6(a). The conventional B-mode image data was taken from the digital output of an image storage device that received the image data from a scan converter. The digital output of the image storage device was copied to a memory associated with an off-line processor. The off-line processor, running a surface-rendering program residing in a MATLAB® program library, generated the surface-rendered image. The MATLAB® program library is commercially available from a software company, The MathWorks, Inc., located in Natick, Mass. The following is a listing, with commentary, of the MATLAB® code used to generate the surface-rendered image shown in FIG. 6(b):

load img "load scan converted image"

Y=conv2([1 3 3 1]/8, [1 3 3 1]/8, img, 'same'); "low-pass filter the image"

surf(Y); "generate a surface"

shading interp; "use interpolation for shading"

axis('ij'); axis tight; view(180, 87); "adjust the image orientation"

set(gca, 'vis','off'); "turn off extraneous graphics"

colormap(gray(255)); caxis([5, 150]); "define the color mapping"

The information contained in FIG. 6(b) is more easily discerned and interpreted than the information in the conventional image shown in FIG. 6(a). In particular, the anterior wall, the inter-ventricular septum, the bright "T" shaped aortic valve, and the posterior wall of the heart are more easily discerned and interpreted than the identical structures conventionally shown in FIG. 6(a). Furthermore, when a series of images are viewed as a movie, the heart walls and valves appear as moving pieces of tissue, further aiding the user in the interpretation of the image data.

A preferred embodiment of the invention provides a user interface for the user to select a perspective from which to view the mapped 3-D mathematical data set. The user can choose to observe the surface from different angles and/or different distances. Typically, the surface-rendered image is displayed on the same ultrasound display with which the original 2-D ultrasound data set is displayed; or the surface-rendered image may be displayed on a second display integrated with the ultrasound system. In an alternative embodiment of the invention, a personal computer or workstation can be used to surface-render the image, after the data is acquired.

The present invention can also be applied to planar, quasi-planar, or projected data sets that are extracted from a 3-D data set acquired from a plurality of 2-D ultrasound data sets. As is well known in the art, there are many ways to generate such 3-D data sets. For example, such a 3-D data set can be acquired with a 2-D transducer array, or with a 1-D transducer array having a position sensor. Alternatively, a spatially accurate 3-D data set can be generated from a series of 2-D data sets obtained from an ultrasound transducer modified to incorporate multiple arrays. This method is described in co-pending U.S. patent application Ser. No. 08/916,585, filed on Aug. 22, 1997, entitled "Multiple Ultrasound Image Registration System, Method and Transducer," which is assigned to the assignee of the present invention. Yet another alternative generates a spatially accurate 3-D data set from a series of 2-D data sets obtained from an unmodified 1-D ultrasound transducer, as described in co-pending U.S. patent application Ser. No. 09/333,823, filed on Jun. 15, 1999, entitled "3-D Diagnostic Medical Ultrasound Imaging Using a 1-D Array," which is assigned to the assignee of the present invention.

One application involving 3-D imaging and the present invention is directed to locating a tissue/fluid interface (e.g., a heart chamber enclosing blood) or a tissue/tissue interface (e.g., a boundary between two organs) from a 3-D ultrasound data set. First, the 3-D ultrasound data set is acquired from a series of 2-D data sets obtained from an ultrasound transducer. Then a tissue/fluid or tissue/tissue interface is determined from the 3-D ultrasound data set, and a 3-D subset is defined having 3-D coordinates based on the interface. The interface may be determined, for example, by applying an amplitude threshold to the 3-D data set. Preferably, the 3-D data set is filtered, such as with a low pass filter or a median filter, prior to applying the amplitude threshold to the 3-D data set. The interface is the set of points having neighboring points that both exceed and do not exceed the threshold. Then the 3-D coordinates of the interface are mapped to points on a 2-D plane. The points on the 2-D plane are then transformed into a mathematical 3-D data set, which is then transformed into an altered 2-D data set, as previously described.

The exemplary embodiments described herein are for purposes of illustration and are not intended to be limiting. Examples of variations within the scope of this invention include, but are not limited to, the following:

Surface-rendering can be achieved using other algorithms for imaging than those specifically disclosed herein and still achieve the intended benefits of the invention.

Surface-rendering can be performed as a combination of mapping performed by means of one or more look-up tables and calculations by one or more processors.

The mapping of the second parameter can be based on the calculated amount of contrast agent present in a region of tissue.

Rendering and display is preferably accomplished in or close to "real time"; however, non-real time embodiments, including off-line processing, are also within the scope of the invention.

Moreover, one of skill in the art will appreciate that the system block diagram of FIG. 1 is intended to be illustrative and not limiting. Specific details of implementation can be varied without departing from the scope of the invention. For example, the signal processor and acquisition controller can be optionally integrated into a single processor, and there can also be integration of the optional remote processor and image storage functions in the main signal path of the system. System 100 is merely an example of a generic ultrasound system configuration. Many variations of such an ultrasound system can be used in carrying out this invention. In fact, any commercial ultrasound platform can be used, including but not limited to: Acuson's Sequoia® and Aspen™ platforms; Philips/ATL's HDI® platforms; General Electric's LOGIQ™ platforms; Toshiba's PowerVision™ platforms; Hewlett-Packard's Sonos™ platforms; Siemen's Sonoline® and Elegra™ platforms; and the like. The instant invention does not depend on the specific type of ultrasound platform or transducer used, but rather, is directed to the manner in which ultrasound data is processed and/or displayed.

Therefore, those skilled in the art will recognize that other embodiments could be practiced without departing from the scope and spirit of the claims set forth below.

What is claimed is:

1. A method for converting 2-D ultrasound data, comprising the steps of:
   (a) inputting a 2-D ultrasound data set;
   (b) transforming the 2-D ultrasound data set into a mathematical 3-D data set; and
   (c) transforming the mathematical 3-D data set into an altered 2-D data set.

2. The method of claim 1, wherein the step of transforming the 2-D ultrasound data set comprises extracting an ultrasound parameter from the 2-D ultrasound data set.

3. The method of claim 1, wherein the step of transforming the mathematical 3-D data set comprises applying a color value to each point on a displayed image, and the color value represents a first or second parameter derived from the 2-D ultrasound data set.

4. The method of claim 1, wherein the 2-D ultrasound data set in step (a) is input based on information obtained from one frame of ultrasound data.

5. The method of claim 1, wherein the 2-D ultrasound data set in step (a) is input based on information obtained from one frame of ultrasound data derived from a 3-D ultrasound data set.

6. The method of claim 1, wherein the 2-D ultrasound data set in step (a) is input based on information obtained from the ultrasound data of one or more ultrasound M-mode lines.

7. A system for converting 2-D ultrasound data, comprising:
   (a) means for acquiring a 2-D ultrasound data set;
   (b) means for transforming the 2-D ultrasound data set into a mathematical 3-D data set; and
   (c) means for transforming the mathematical 3-D data set into an altered 2-D data set.

8. The system of claim 7, wherein the means for transforming the 2-D ultrasound data set extracts an ultrasound parameter from the 2-D ultrasound data set.

9. The system of claim 7, wherein the means for transforming the mathematical 3-D data set applies a color value to each point on a displayed image, and the color value represents a first or second parameter derived from the 2-D ultrasound data set.

10. The system of claim 7, wherein both means for transforming comprise a digital signal processor.

11. A method for converting a 2-D ultrasound data set into an altered 2-D display image, comprising the steps of:
   (a) generating a mathematical surface of a plurality of 3-D coordinates, wherein the height of the mathematical surface is based on a first component of an ultrasound signal in the 2-D ultrasound data set;
   (b) mapping the mathematical surface to points on a 2-D plane;
   (c) assigning a color value to each point based on a second component of the ultrasound signal; and
   (d) displaying the mapped mathematical surface of step b) with the assigned color values of step (c) on a 2-D display device.

12. The method of claim 11, wherein the mapping step (b) comprises projecting the mathematical surface to points on a 2-D plane.

13. The method of claim 11, wherein the 2-D ultrasound data set is a M-mode data set, and one component of the 2-D ultrasound data set represents a time variable.

14. The method of claim 11, further comprising, before step (a), acquiring the 2-D ultrasound data set with a 1-D phased array ultrasound transducer.

15. The method of claim 11, further comprising, before step (a), acquiring the 2-D ultrasound data set with a single crystal ultrasound transducer.

16. The method of claim 11, further comprising, before step (a), acquiring the 2-D ultrasound data set with a 2-D phased array ultrasound transducer.

17. The method of claim 11, wherein the first component and the second component are the same component of the ultrasound signal in the 2-D ultrasound data set.

18. The method of claim 11, wherein the first component and the second component are different components of the ultrasound signal in the 2-D ultrasound data set.

19. The method of claim 11, further comprising, before step (a), deriving the 2-D ultrasound data set from a 3-D ultrasound data set.

20. The method of claim 11, wherein the surface height and pixel color value are functions of the same parameters.

21. The method of claim 11, wherein the ultrasound data set includes B-mode data.

22. The method of claim 11, wherein the ultrasound data set includes color Doppler data.

23. The method of claim 11, wherein the ultrasound data set includes color Doppler and B-mode data.

24. The method of claim 11, wherein the first component is a function of the energy of Doppler signals, and the second component is a function of the velocity estimate of the Doppler signals.

25. The method of claim 22, wherein the ultrasound data set includes color is Doppler data, and the mathematical surface height is a function of either the energy, the velocity, the variance, or combination thereof, of the Doppler data.

26. The method of claim 11, wherein the ultrasound data set includes color Doppler data and the color is a function of the Doppler energy, velocity, variance, or any combination thereof.

27. The method of claim 11, wherein the ultrasound data set includes color M-mode data.

28. The method of claim 11 further comprising the step of providing a user interface for a user to select an angle or distance from which to view the mapped mathematical surface.

29. The method of claim 11, wherein the steps are performed as the 2-D ultrasound data is being collected.

30. The method of claim 11, wherein the steps are performed after the 2-D ultrasound data is stored in memory.

31. The method of claim 11, wherein the color value is a function of a reflectivity of the mathematical surface and the relative positions of a light source, a user, and the geometric normal to the mathematical surface at each point on the mathematical surface.

32. A method for converting a 3-D ultrasound data set into a 2-D data set, comprising the steps of:
   acquiring a 3-D ultrasound data set from a series of 2-D data sets;
   locating a tissue/fluid or tissue/tissue interface from the 3-D ultrasound data set, and defining a 3-D subset having 3-D coordinates based on said interface;
   mapping the 3-D coordinates of the interface to points on a 2-D plane;
   transforming the points into a mathematical 3-D data set; and
   transforming the mathematical 3-D data set into an altered 2-D data set.

33. The method of claim 32, further comprising the step of assigning a color value to each point based on a component of the ultrasound signal at the interface.

34. The method of claim 33, wherein the component of the ultrasound signal is the energy within a frequency sub-band of the ultrasound signal.

35. The method of claim 34, wherein the component of the ultrasound signal is the energy within a fundamental, harmonic, sub-harmonic or ultra-harmonic frequency sub-band of the ultrasound signal.

36. The method of claim 33, wherein the component of the ultrasound signal is an estimate of the amount of the contrast agent present.

37. The method of claim 33, wherein the component of the ultrasound signal is based on localized image statistics.

38. The method of claim 33, wherein the step of assigning a color value to each point is based on the correlation of the localized signals.

39. The method of claim 33, wherein the step of assigning a color value to each point is based on a function including a light source and/or a reflectivity of the surface, and the relative positions of the light source, a user, and the geometric normal to the surface at each point.

40. A diagnostic medical ultrasound system for converting a 2-D ultrasound data set into a 2-D display image, comprising:
   (a) means for generating a mathematical surface of a plurality of 3-D coordinates from the 2-D ultrasound data set, wherein the height of the mathematical surface is based on a first component of the ultrasound data set;
   (b) means for mapping the mathematical surface to points on a 2-D plane;
   (c) means for assigning a color value to each point based on a second component of the ultrasound data set; and
   (d) means for displaying the mapped mathematical surface of step (b) with the assigned color values of step (c) on a 2-D display device.

41. The system of claim 40, further comprising means for performing the mapping of step (b) as a projection of the mathematical surface to points on a 2-D plane.

42. The system of claim 40, wherein the 2-D ultrasound data set is M-mode data and one component of the 2-D ultrasound data set represents a time variable.

43. The system of claim 40, further comprising a phased array ultrasound transducer for acquiring the data set.

44. The system of claim 40, further comprising a single crystal ultrasound transducer for acquiring the data set.

45. The system of claim 40, further comprising a 2-D phased array ultrasound transducer for acquiring the data set.

46. The system of claim 40, wherein the first component and the second component are the same.

47. The system of claim 40, wherein the first component and the second component are different.

48. The system of claim 40, wherein the 2-D ultrasound data set is derived from a 3-D ultrasound data set.

49. The system of claim 48, wherein the 2-D ultrasound data is based on a mathematical projection of the 3-D ultrasound data into a 2-D ultrasound data, and the amplitude and color value of a derived 2-D display image is a function of the 3-D ultrasound data.

50. The system of claim 40, wherein the surface height and pixel color value are functions of the same parameter or parameters.

51. The system of claim 40, wherein the ultrasound data set comprises B-mode data.

52. The system of claim 40, wherein the ultrasound data set comprises color Doppler data.

53. The system of claim 40, wherein the ultrasound data set comprises both color Doppler data and B-mode data.

54. The system of claim 40, wherein the first component is a function of the energy of Doppler data and the second component is a function of the velocity estimate of the Doppler data.

55. The system of claim 40, wherein the ultrasound data set includes color Doppler data and the surface height is a function of either the energy, the velocity, the variance, or combination thereof, of the Doppler data.

56. The system of claim 40, wherein the ultrasound data set includes color Doppler data and the color is a function of the Doppler energy, velocity, variance, or any combination thereof.

57. The system of claim 40, wherein the ultrasound data set includes color m-mode data.

58. The system of claim 40, further comprising a user interface for a user to select an observation perspective of the surface.

59. The system of claim 43, wherein the means for displaying is an auxiliary display distinct from the ultrasound system that displays the mapped mathematical surface within 20 seconds after the 2-D ultrasound data set is acquired by the transducer.

60. The system of claim 40, wherein the means for displaying is an auxiliary display distinct from the ultrasound system display.

61. The system of claim 40, wherein the color value is based on a function of the reflectivity of the mathematical surface and the relative positions of a light source, a user, and the geometric normal to the mathematical surface at each point on the mathematical surface.

62. A diagnostic medical ultrasound system for converting a 3-D ultrasound data set into a 2-D data set, comprising:
   means for acquiring a 3-D ultrasound data set from a series of 2-D data sets;
   means for locating a tissue/fluid or tissue/tissue interface from the 3-D data set, and defining a 3-D subset having 3-D coordinates based on said interface;
   means for mapping the 3-D coordinates of the interface to points on a 2-D plane;
   means for transforming the points into a mathematical 3-D data set; and
   means for transforming the mathematical 3-D data set into an altered 2-D data set.

63. The system of claim 62, further comprising means for assigning a color value to each point based on a component of the ultrasound signal at the interface.

64. The system of claims 40 or 63, further comprising means for assigning a color value to each point based on the energy within a frequency sub-band of the ultrasound signal.

65. The system of claim 64, further comprising means for assigning a color value to each point based on the energy within a fundamental, harmonic, sub-harmonic or ultra-harmonic frequency sub-band of the ultrasound signal.

66. The system of claims 40 or 63, further comprising means for assigning a color value to each point based on an estimate of the amount of the contrast agent present.

67. The system of claims 40 or 63, further comprising means for assigning a color value to each point based on localized image statistics.

68. The system of claims 40 or 63, further comprising means for assigning a color value to each point based on the correlation of the localized signals.

69. The system of claim 63, further comprising means for assigning a color value to each point as a function of a light source and/or a reflectivity of the surface, and the relative positions of the light source, a user, and the geometric normal to the surface at each point.

* * * * *